United States Patent [19]

Walker

[11] Patent Number: 5,712,124
[45] Date of Patent: *Jan. 27, 1998

[54] STRAND DISPLACEMENT AMPLIFICATION

[75] Inventor: George Terrance Walker, Chapel Hill, N.C.

[73] Assignee: Becton, Dickinson and Company, Franklin Lakes, N.J.

[*] Notice: The term of this patent shall not extend beyond the expiration date of Pat. No. 5,270,184.

[21] Appl. No.: 375,133

[22] Filed: Jan. 18, 1995

Related U.S. Application Data

[63] Continuation-in-part of Ser. No. 819,358, Jan. 9, 1992, Pat. No. 5,455,166, which is a continuation-in-part of Ser. No. 648,257, Jan. 31, 1991, abandoned.

[51] Int. Cl.$^6$ .................................................. C12P 19/34
[52] U.S. Cl. .................................... 435/91.2; 435/6
[58] Field of Search ............................ 435/6, 91.2

[56] References Cited

U.S. PATENT DOCUMENTS 5,270,184  12/1993  Walker ............................ 435/91.2

OTHER PUBLICATIONS

Taylor et al. Nucleic Acids Res. 13(24):8749–8764, 1985.

*Primary Examiner*—Scott W. Houtteman
*Attorney, Agent, or Firm*—Donna R. Fugit

[57] ABSTRACT

This invention relates a nucleic acid target amplification and detection method which operates at a single temperature and makes use of a polymerase in conjunction with an endonuclease that will nick the polymerized strand such that the polymerase will displace the strand without digestion while generating a newly polymerized strand.

23 Claims, 2 Drawing Sheets

STRAND DISPLACEMENT AMPLIFICATION

CROSS REFERENCE TO RELATED APPLICATIONS

This patent application is a continuation-in-part of parent application Ser. No. 07/819,358, filed Jan. 9, 1992, now U.S. Pat. No. 5,455,166 which is a continuation-in-part of patent application Ser. No. 07/648,257, filed Jan. 31, 1991, now abandoned.

FIELD OF THE INVENTION

This invention relates to a method for amplifying a target nucleic acid sequence, and more particularly relates to a method for amplification by endonuclease mediated strand displacement and detection of the amplified reaction product(s).

BACKGROUND OF THE INVENTION

Nucleic acids may be either in the form of deoxyribonucleic acids (DNA) or in the form of ribonucleic acids (RNA). DNA and RNA are high molecular weight polymers formed from many nucleotide building blocks. Each nucleotide is composed of a base (a purine or a pyrimidine), a sugar (either ribose or deoxyribose) and a molecule of phosphoric acid. DNA is composed of the sugar deoxyribose and the bases adenine (A), guanine (G), cytosine (C) and thymine (T).

The nucleotides are assembled into a linear chain to form the genetic code. Each sequence of three nucleotides can be "read" as the code for one amino acid through the process of translation. (DNA must first be converted into RNA through the process of transcription.) By varying the combination of bases in each three base sequence, different amino acids are coded for. By linking various three base sequences together, a sequence of amino acids can be made which form proteins. The entire coding unit for one protein is referred to as a gene. There can be one or more copies of a gene in an organism. Some genes are present in hundreds or thousands of copies. Others are present only as a single copy. Regardless of the number of copies, genes are linked together in an organism to form higher structural units referred to as chromosomes in higher organisms. In some lower organisms, genes may occur in extra chromosomal units referred to as plasmids. Genes need not be linked directly to each other in an end-to-end fashion. Certain non-coding regions (i.e., sequences of bases that do not translate into amino acids) may occur between genes or within a gene. Thus, the arrangement of nucleotides in an organism determines its genetic makeup which may be referred to as its genome. (Hence, DNA isolated from an organism is referred to as genomic DNA.)

DNA in most organisms is arranged in the form of a duplex wherein two strands of DNA are paired together in the familiar double helix. In this model, hydrogen bonds are formed between A and T and between C and G on the paired strands. Thus, on one strand, the sequence ATCG (5'→3') will have on its complementary strand the sequence TAGC (3'→5'). Both strands, however, contain the same genetic code only in a complementary base-paired manner. One could read, therefore, either strand of DNA in order to determine the genetic sequence coded for. For a further description of the organization, structure and function of nucleic acids, see Watson, *Molecular Biology of the Gene*, W. J. Benjamin, Inc. (3rd edit. 1977), especially chs. 6–14.

Understanding and determining the genetic sequence of nucleic acids present in a sample is important for many reasons. First, a number of diseases are genetic in the sense that the nucleotide sequence for a "normal" gene is in some manner changed. Such a change could arise by the substitution of one base for another. Given that three bases code for a single amino acid, a change in one base (referred to as a point mutation) could result in a change in the amino acid which, in turn, could result in a defective protein being made in a cell. Sickle cell anemia is a classic example of such a genetic defect caused by a change in a single base in a single gene. Other examples of diseases caused by single gene defects include Factor IX and Factor VIII deficiency, adenosine deaminase deficiency, purine nucleotide phosphorylase deficiency, ornithine transcarbamylase deficiency, argininsuccinate synthetase deficiency, beta-thalassemia, $\alpha_1$ antitrypsin deficiency, glucocerebrosidase deficiency, phenylalanine hydroxylase deficiency and hypoxanthine-guanine phosphoribosyltransferase deficiency. Still other diseases, such as cancers, are believed to be caused by the activation, increase in copy number and/or removal of suppression of genes known to be present in the genome referred to as oncogenes. Examples of oncogenes believed to be relevant to certain cancers include N-myc for neuroblastomas, retinoblastomas and small-cell lung cancers and c-abl for chronic myelogenous leukemia. For a further description of the relevance of oncogenes to the diagnosis of cancers and for a listing of specific oncogenes, see Weinberg, Sci. Amer., Nov. 1983, Slamon et al., Science, 224:256 (1984), U.S. Pat. No. 4,699,877 and 4,918,162.

Second, in addition to changes in the sequence of nucleic acids, there are genetic changes that occur on a structural level. Such changes include insertions, deletions and translocations along a chromosome and include increased or decreased numbers of chromosomes. In the former instance, such changes can result from events referred to as crossing-over where strands of DNA from one chromosome exchange various lengths of DNA with another chromosome. Thus, for example, in a "normal" individual, the gene for protein "X" might reside on chromosome 1; after a crossing-over event, that gene could now have been translocated to chromosome 4 (with or without an equal exchange of DNA from chromosome 4 to chromosome 1) and the cell may not produce X. In the instance of increased or decreased chromosome number (referred to as aneuploidy), instead of a "normal" individual having the correct number of copies of each chromosome (e.g., two of each in humans [other than the X and Y chromosomes]), a different number occurs. In humans, for example, Down's syndrome is the result of having three copies of chromosome 21 instead of the normal two copies. Other aneuploid conditions result from trisomies involving chromosomes 13 and 18.

Third, infectious diseases can be caused by parasites, microorganisms and viruses all of which have their own nucleic acids. The presence of these organisms in a sample of biological material often is determined by a number of traditional methods (e.g., culture). Because each organism has its own genome, however, if there are genes or sequences of nucleic acids that are specific to a single species (to several related species, to a genus or to a higher level of relationship), the genome will provide a "fingerprint" for that organism (or species, etc.). Examples of viruses to which this invention is applicable include HIV, HPV, EBV, HSV, Hepatitis B and C and CMV. Examples of microorganisms to which this invention is applicable include bacteria and more particularly include *H. influenzae*, mycoplasma, legionella, mycobacteria, chlamydia, candida, gonocci, shigella and salmonella.

In each example set forth above, by identifying one or more sequences that are specific for a disease or organism, one can isolate nucleic acids from a sample and determine if that sequence is present. A number of methods have been developed in an attempt to do this.

While it is critical that one or more sequences specific for a disease or organism be identified, it is not important to the practice of this invention what the target sequences are or how they are identified. The most straightforward means to detect the presence of a target sequence in a sample of nucleic acids is to synthesize a probe sequence complementary to the target nucleic acid. (Instrumentation, such as the Applied BioSystems 380B, are presently used to synthesize nucleic acid sequences for this purpose.) The synthesized probe sequence then can be applied to a sample containing nucleic acids and, if the target sequence is present, the probe will bind to it to form a reaction product. In the absence of a target sequence and barring non-specific binding, no reaction product will be formed. If the synthesized probe is tagged with a detectable label, the reaction product can be detected by measuring the amount of label present. Southern blotting is one example where this method is used. A difficulty with this approach, however, is that it is not readily applicable to those instances where the number of copies of the target sequence present in a sample is low (i.e., less than $10^7$). In such instances, it is difficult to distinguish signal from noise (i.e., true binding between probe and target sequences from non-specific binding between probe and non-target sequences). One way around this problem is to increase the signal. Accordingly, a number of methods have been described to amplify the target sequences present in a sample.

One of the best known amplification methods is the polymerase chain reaction (referred to as PCR) which is described in detail in U.S. Pat. Nos. 4,683,195, 4,683,202 and 4,800,159. Briefly, in PCR, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products, and the process is repeated.

Another method for amplification is described in EPA No. 320,308, published Jun. 14, 1989, which is the ligase chain reaction (referred to as LCR). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence but does not describe an amplification step.

A still further amplification method is described in PCT Appl. No. PCT/US87/00880, published Oct. 22, 1987, and is referred to as the Qbeta Replicase method. In this method, a replicative sequence of RNA which has a region complementary to that of a target is added to a sample in the presence of an RNA polymerase. The polymerase will copy the replicative sequence which then can be detected.

Still other amplification methods are described in GB Appl. No. 2 202 328, published Sep. 21, 1988, and in PCT Appl. No. PCT/US89/01025, published Oct. 5, 1989. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence.

For all of the above-described methods, a variety of detection methods may be employed, none of which is critical to the amplification method employed. One method is to detect reaction products having a specific size via electrophoresis. Another method is to radiolabel the primer sequence with $^{32}$P, for example, and then to detect the radioactivity emitted by the reaction products alone or in combination with electrophoresis. A further method is to chemically modify the primer by adding a receptor having a ligand (e.g., biotin-avidin), and enzyme (e.g., alkaline phosphatase), a fluorescent dye (e.g., phycobiliprotein) or a combination. Another method is to develop a detection primer which will bind to the reaction product and be extended in the presence of polymerase. The detection primer can be radiolabelled or chemically modified as described above. Many of these methods may be adapted to solid phase as well as solution systems. A number of these methods, as well as others, are described in U.S. Pat. Nos. 4,358,535, 4,705,886, 4,743,535, 4,777,129, 4,767,699, and 4,767,700.

Each of the above-referenced amplification methods has one or more limitations. In most of the amplification methods, a key limitation is the requirement for temperature cycling to cause the reaction products to dissociate from the target. This places a limitation on both the devices used to perform the method as well as on the choice of enzymes necessary to form the reaction products. Other limitations of these methods include production of RNA intermediates sensitive to endogenous nuclease degradation and difficulty in production of associated enzymes. Alternative methods to such existing amplification methods are desirable.

SUMMARY OF THE INVENTION

This invention provides for a method of amplification of a target nucleic add sequence (and its complementary strand) in a sample by endonuclease mediated strand displacement. The method involves the steps of 1) isolating nucleic acids suspected of containing the target sequence from a sample, 2) generating single stranded fragments of target sequences, 3) adding a mixture comprising (a) a nucleic acid polymerase, (b) deoxynucleoside triphosphates including at least one substituted deoxynucleoside triphosphate and (c) at least one primer which is complementary to a region at the 3' end of a target fragment and further wherein each primer has a sequence at the 5' end which is a recognition sequence for a restriction endonuclease, and 4) allowing the mixture to react for a time sufficient to generate reaction products. Where the fragments comprise double stranded nucleic acids, the method further comprises denaturing the nucleic acid fragments to form single stranded target sequences. Where the nucleic acids comprise RNA, it is preferable to use reverse transcriptase to convert RNA to DNA.

The invention further relates to methods for the separation and/or detection of reaction products generated by the above-described method. Methods for separation comprise magnetic separation, membrane capture and capture on solid supports. In each method, a capture moiety may be bound to a magnetic bead, membrane or solid support. The beads, membrane or solid support then can be assayed for the presence or absence of reaction products. An example of a capture moiety includes a nucleic acid sequence complementary to the reaction products produced and an antibody directed against a receptor incorporated into the primer or reaction product. The separation system may or may not be coupled to a detection system.

Detection systems useful in the practice of this invention comprise homogeneous systems, which do not require separation, and heterogeneous systems. In each system, one or more detectable markers are used and the reaction or emission from the detection system is monitored, preferably by automated means. Examples of homogeneous systems include fluorescence polarization, enzyme mediated immunoassays, fluorescence energy transfer, hybridization protection (e.g., acridinium luminescence) and cloned enzyme donor immunoassays. Examples of heterogeneous systems include enzyme labels (such as peroxidase, alkaline phosphatase and beta-galactosidase), fluorescent labels (such as enzymatic labels and direct fluorescence labels [e.g., fluorescein and rhodamine]), chemiluminescence and bioluminescence. Liposomes or other sac like particles also can be filled with dyes and other detectable markers and used in such detection systems. In these systems, the detectable markers can be conjugated directly or indirectly to a capture moiety or the reaction products can be generated in the presence of a receptor which can be recognized by a ligand for the receptor.

The invention further relates to methods of generating amplified products which can function as probes or templates for sequence analysis. In this format, the above described method and steps are used to generate amplified products. The amplified products can then be treated to remove the nicking enzyme recognition sequence from the amplified product, for example by using a restriction enzyme. In this manner, the recognition sequence is removed and the remaining amplified product comprises a probe which can be used in other systems.

In the presence of a single stranded target fragment, a primer will bind to its complementary target strand. In the presence of polymerase, nucleotides and substituted nucleotides will be added to the 3' end of the primer along the remaining length of the target and nucleotides and substituted nucleotides will be added to the 3' end of the target along the primer sequence. The resulting double stranded product will have one sequence containing substituted nucleotides coupled to the 3' end of the target strand while the primer strand will have an unmodified sequence coupled 5' to an extended sequence complementary to the target sequence. The endonuclease then cleaves the recognition sequence on the primer strand but does not cleave the complementary sequence on the target strand because its sequence contains the substituted nucleotides. The polymerase extends the 3' end at the nick and simultaneously displaces the downstream strand 5' to the nick generating a reaction product complementary to the target strand.

The method also can function with two primers wherein one primer will bind to one strand of a target sequence and the other primer will bind to the complementary strand of the target sequence. When this embodiment is used, it will be apparent that each reaction product can function as a "target" for the other primer. In this manner, amplification proceeds logarithmically.

As used in this document, "nicking" refers to preferential cleavage of one of two strands present in a double-stranded recognition site.

DETAILED DESCRIPTION

Figure 1:
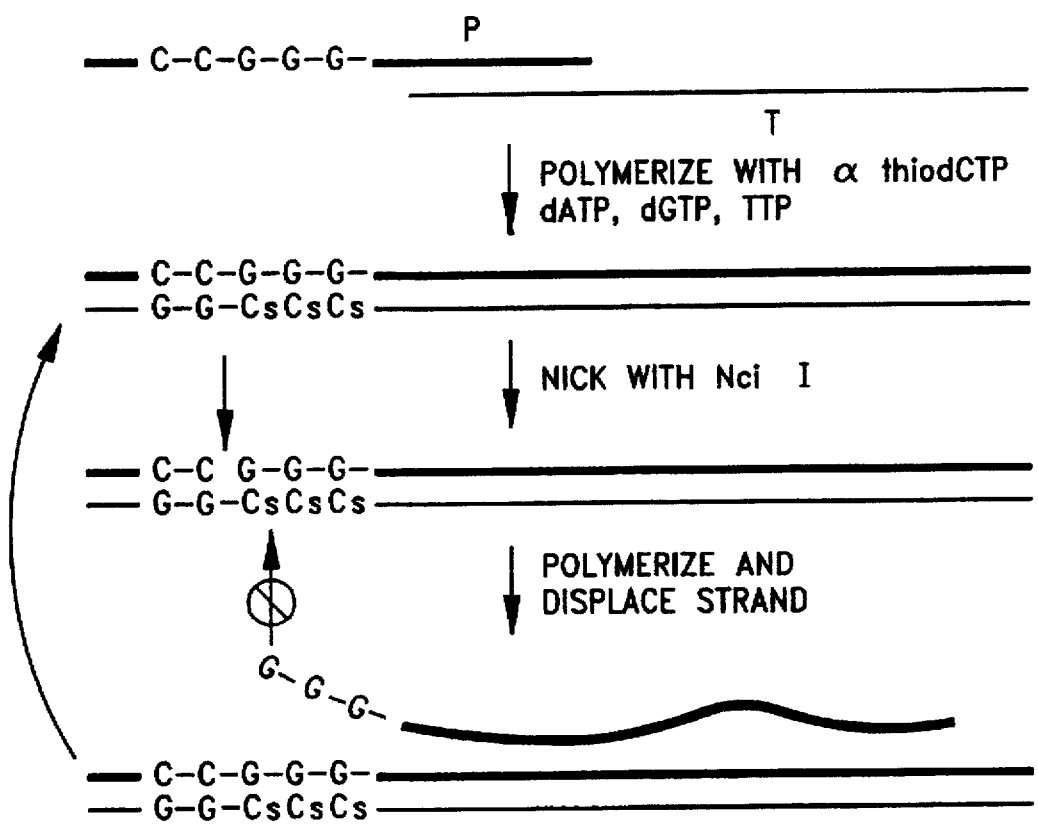
FIG. 1 comprises a flow chart of the steps in an example of the method claimed in this invention for a single stranded DNA fragment and one amplification primer.

In this invention, the sample may be isolated from any material suspected of containing the target nucleic acid sequence. For animals, preferably, mammals, and more preferably humans, the sources of such materials may comprise blood, bone marrow, lymph, hard tissues (e.g., liver, spleen, kidney, lung, ovary, etc.), sputum, feces and urine. Other sources of material may be derived from plants, soil and other materials suspected of containing biological organisms. The isolation of nucleic acids from these materials can be done any number of ways. Such methods include the use of detergent lysates, sonication, vortexing with glass beads and a French press. In some instances, it may be advantageous to purify the nucleic acids isolated (e.g., where endogenous nucleases are present). In those instances, purification of the nucleic acids may be accomplished by phenol extraction, chromatography, ion exchange, gel electrophoresis or density dependent centrifugation.

Once the nucleic acids are isolated, it will be assumed for purposes of illustration only that the genomic nucleic acid is DNA and is double stranded. In such instances, it is preferred to cleave the nucleic acids in the sample into fragments of between approximately 50–500 bp. This may be done by a restriction enzyme such as HhaI, FokI or DpnI. The selection of the enzyme and the length of the sequence should be such so that the target sequence sought will be contained in its entirety within the fragment generated or at least a sufficient portion of the target sequence will be present in the fragment to provide sufficient binding of the primer sequence. Other methods for generating fragments include PCR and sonication.

The primers used in this method generally have a length of 25–100 nucleotides. Primers of approximately 35 nucleotides are preferred. This sequence should be substantially homologous to a sequence on the target such that under high stringency conditions binding will occur. The primer also should contain a sequence (toward the 5' end) that will be recognized by the nicking endonuclease to be used in later steps. The recognition sequences generally, although not necessarily, are non-palindromic. The sequence selected also may be such that the restriction enzyme used to cleave the fragments in the previous step is the same as the nicking endonuclease to be used in later steps.

Once target nucleic acid fragments are generated, they are denatured to render them single stranded so as to permit binding of the primers to the target strands. Raising the temperature of the reaction to approximately 95° C. is a preferred method for denaturing the nucleic acids. Other methods include raising pH; however, this will require lowering the pH in order to allow the primers to bind to the target. Either before or after the nucleic acids are denatured, a mixture comprising an excess of all four deoxynucleoside triphosphates (dNTPs), wherein at least one of the dNTPs is substituted, a polymerase and an endonuclease are added. (If high temperature is used to denature the nucleic acids, unless thermophilic enzymes are used, it is preferrable to add the enzymes after denaturation.) The substituted deoxynucleoside triphosphate should be modified such that it will inhibit cleavage of the primer strand containing the substituted deoxynucleotides but will not inhibit cleavage on the other primer strand. Examples of such substituted deoxynucleoside triphosphates include 2'-deoxyadenosine 5'-O-(1-thiotriphosphate), 5-methyldeoxycytidine 5'-triphosphate, 2'-deoxyuridine 5'-triphosphate and 7-deaza-2'-deoxyguanosine 5'-triphosphate. Alternatively, the substituted deoxynucleoside triphosphate may inhibit cleavage of the primer strand which does not contain the substitution, allowing cleavage of the primer strand which is modified.

It should be appreciated that the substitution of the deoxynucleotides may be accomplished after incorporation into a strand. For example, a methylase, such as M. Taq I, could be used to add methyl groups to the synthesized strand. The methyl groups, when added to the nucleotides, are thus substituted and will function in similar manner to the thio substituted nucleotides. It further should be appreciated that if all the nucleotides are substituted, then the polymerase need not lack the 5'→3' exonuclease activity. The presence of the substituents throughout the synthesized strand will function to prevent such activity without inactivating the system.

As described for the selection of the recognition sequence incorporated in the primer, the selection of the endonuclease used in this method should be such that it will cleave a strand at or 3' (or 5') to the recognition sequence. The endonuclease further should be selected so as not to cleave the complementary recognition sequence that will be generated in the target strand by the presence of the polymerase, and further should be selected so as to dissociate from the nicked recognition sequence at a reasonable rate. It need not be thermophilic. Endonucleases, such as HincII, HindII, AvaI, Fnu4HI, Tth111I, and NciI are preferred. One can also envision several alternative nicking enzyme systems. For example, it is generally regarded that class IIS restriction endonucleases (e.g., FokI) contain two DNA cleavage centers within a single polypeptide unit. If one of the cleavage centers was inactivated, such as through site directed mutagenesis, the resultant nicking enzyme could be used in an amplification system not requiring modified deoxynucleoside triphosphates. As an additional example, the restriction enzyme EcoRI has been shown to preferentially cleave one strand in noncanonical recognition sites or when its canonical recognition site is flanked by an oligopurine tract (Thielking et al. (1990) Biochemistry 29, 4682; Lesser et al. (1990) Science 250, 776; Venditti & Wells (1991) J. Biol. Chem. 266, 16786). As another example, the restriction enzyme DpnI (available from New England Biolabs, Beverly Mass.) cleaves a recognition site containing me$^6$dA on both strands. DpnI or an analogous restriction enzyme (e.g., Fnu4HI or ScrfI) may be able to nick the methyl containing strand of a hemimethylated recognition site. Such a system would employ SDA primers ($P_1$ and $P_2$) with methylated recognition sequences along with unmodified deoxynucleoside triphosphates. Alternatively, certain restriction enzymes are known to cleave the nonmethylated strand of a hemimethylated recognition site (e.g., MspI and me$^5$dC). Such a system would use a methylated deoxynucleoside triphosphate. Finally, one could use origin of replication proteins to nick one strand of a recognition sequence.

The utility of a restriction endonuclease in the Strand Displacement Amplification methods of the invention can be predicted using a "strand protection" assay which assesses the ability of the restriction endonuclease to nick one strand of a hemimodified recognition site for the restriction endonuclease. Such nicking activity is essential for the restriction endonuclease to be useful in SDA, as the polymerase requires the nick in order to generate copies of the target sequence (i.e., the amplification products). In the strand protection assay, double stranded oligonucleotides containing hemimodified recognition sequences for the restriction endonucleases were constructed as follows. Template strands comprising the appropriate recognition sites for the endonucleases and primers which hybridized to the templates were synthesized and purified by gel electrophoresis with electroelution from gel slices using standard methods. To screen multiple restriction endonucleases using a single template, multiple cleavage sites were positioned on the templates such that nicking or double stranded cleavage of each site would result in a fragment which could be distinguished by size on a gel. The template strands and primers were then separately 5' end-labeled using T4 polynucleotide kinase and γ-[$^{32}$P]-adenosine triphosphate for later autoradiographic detection. A typical kinase reaction contained 2 μL of 10X kinase buffer (New England Biolabs), 10 μL of γ-[$^{32}$P]-ATP (3000 curies/mmol, NEN-DuPont), primer or template to give a final concentration of 1 μM, 20 units T4 polynucleotide kinase (New England Biolabs), and water to make a total reaction volume of 20 μL. Kinase reactions were performed at 37° C. for 30 min., then terminated by heating in boiling water for 5 min.

The 5' end-labeled primer was then hybridized to the 5' end-labeled template strand and extended with polymerase in the presence of the substituted deoxynucleoside triphosphate to be tested, producing a double-stranded oligonucleotide in which the recognition/cleavage sites were hemimodified. Derivatized dNTPs were incorporated into one or the other of the two strands of the recognition/cleavage sites in different experiments to test the effect on nicking activity. To produce the double-stranded oligonucleotide, the radiolabeled primer and template were then annealed by mixing 2 μL of each, 1 μL of REACT-1 buffer (Life Technologies), and 11.5 μL of deionized, distilled water in a closed 0.5 mL polypropylene microfuge tube. This mixture was heated for 3 min. in a boiling water bath, then allowed to cool slowly to 37° C. by removing the water bath from the heat source. The tubes were then transferred to a 37° C. incubator and the hybridized primers were extended on the template by adding 1 μL of the appropriate mix of deoxynucleoside triphosphates (dNTPs) including at least one substituted dNTP, 2 μL of 10 mM dithiothreitol (DTT), and 0.5μL of a 10 unit/μL solution of exonuclease deficient Klenow polymerase (U.S. Biochemicals). The final concentration of each dNTP in the extension reaction was 250 μM. Primer extension reactions were allowed to proceed for 20 min. and were then terminated by heating at 75° C. for 10 min.

After extension, aliquots of the extension reaction were diluted 10-fold into the appropriate buffer for restriction endonuclease activity as recommended by the supplier of the restriction endonuclease. The final concentration of DNA molecules in the assay was 10 nM. Strand protection assays were initiated by adding 5–10 units of the appropriate restriction endonuclease to each reaction mix. The reactions were incubated at the temperature recommended by the supplier of the restriction endonuclease. Samples were removed at regular intervals and added to an equal volume of formamide sequencing reaction stop solution (U.S. Biochemicals) to quench the reaction. Quenched samples were stored on ice until all were collected. The samples were then heated in a boiling water bath for 3 min. and loaded onto 8% polyacrylamide, 7M urea DNA sequencing gels in Tris-borate buffer (Gibco-BRL). Electrophoresis was performed at a constant power level of 57 W for 1 hour. Radiolabeled DNA bands were visualized by autoradiography using Fuji RX grade x-ray film. Presence or absence of nicking activity, and which strand was nicked, was determined by analysis of the sizes of the bands produced.

The restriction endonucleases listed in the following Table were found to nick the indicated recognition sequences when the modified dNTP shown in the last column was incorporated into one of the two strands. No substituted deoxynucleoside triphosphates were found which induced nicking by NlaIII, Asp700, EcoNI, BspMI, HaeII, or NspIII in the strand protection assay. ScrfI nicked its recognition site more efficiently when 5'Me(dCTP) was incorporated than when α-thio dCTP was incorporated.

| ENZYME | RECOGNITION SITE (5'-3') | MODIFIED dNTP |
|---|---|---|
| HincII | GTTGAC | dATP(αS) |
| HincII | GTCAAC | dGTP(αS) |
| AvaI | CCCGAG | TTP(αS) |
| AvaI | CTCGGG | dCTP(αS) |
| NciI | CCGGG | dCTP(αS) |
| HindII | GTTGAC | dATP(αS) |
| HindII | GTCAAC | dGTP(αS) |
| Fnu4HI | GCGGC | dCTP(αS) |
| Fnu4HI | GCGGC | 5'Me(dCTP) |
| BstXI | CCAAAACCCTGG Seq ID No: 15 | TTP(αS) |
| BstXI | CCAGGTTTTGG Seq ID No: 16 | dCTP (αS) |
| BsmI | AAAGCATTC | TTP (αS) |
| BsrI | AACCAGT | TTP (αS) |
| BsaI | GGTCTCTTTTTT Seq ID No: 17 | dATP (αS) |
| NlaIV | GGAACC | TTP (αS) |
| NspI | GCATGT | dCTP (αS) |
| NspI | GCATGT | dCTP (αS) & dGTP (αS) |
| PflMI | CCAGGTTTTGG Seq ID No: 18 | dCTP (αS) |
| HphI | GGTGAGGATCGTTT Seq ID No: 19 | dATP (αS) |
| AlwI | GGATCGTTTTT Seq ID No: 20 | dATP (αS) |
| FokI | GGATGGCATGTCTTTTGGG Seq ID No: 21 | dCTP (αS) |
| AccI | GTAGAC | dCTP (αS) |
| AccI | GTAGAC | TTP (αS) |
| AccI | GTAGAC | TTP (αS) & dCTP (αS) |
| AccI | GTCTAC | dATP (αS) |
| AccI | GTCTAC | dGTP (αS) |
| AccI | GTCTAC | dATP (αS) & dGTP (αS) |
| Tth111I | GACCACGTC | TTP (αS) |
| Tth111I | GACCACGTC | TTP (αS) & dGTP (αS) |
| Tth111I | GACGTGGTC | dCTP (αS) |
| Tth111I | GACGTGGTC | dCTP (αS) & dATP (αS) |
| ScrfI | CCGGG | 5'Me(dCTP) |
| MvaI | CCTGG | dATP(α) |

Six of the endonucleases which nicked in the strand protection assay (HincII, AvaI, NciI, HindII, Fnu4HI and Tth111I) were selected for testing in SDA reactions. All of these restriction endonucleases tested supported target amplification. These results confirm that nicking in the strand protection assay is indicative of the utility of a restriction endonuclease in SDA, particularly when the recognition sequence is non-palindromic as are those listed in the Table. Further, these experiments suggest that other restriction endonucleases which nick a non-palindromic hemimodified recognition sequence in this or a similar assay are likely to support Strand Displacement Amplification, although the rate of amplification may vary considerably depending on the rate of dissociation of the endonuclease from its recognition sequence, buffers, cosolvents, etc.

Polymerases useful in this method include those that will initiate 5'→3' polymerization at a nick site. The polymerase should also displace the polymerized strand downstream from the nick, and, importantly, should also lack any 5'→3' exonuclease activity. Polymerases, such as the klenow fragment of DNA polymerase I and the exonuclease deficient klenow fragment of DNA polymerase I and a similar fragment from the Bst polymerase (Bio-Rad, Richmond, Calif.) are useful. SEQUENASE 1.0 and SEQUENASE 2.0 (US Biochemical), T5 DNA polymerase and Phi29 DNA polymerases also work. It should be appreciated that a polymerase ordinarily having such exonuclease activity can be deemed to "lack" such activity if that activity is blocked by the addition of a blocking agent.

An additional feature of this method is that it does not require temperature cycling. Many amplification methods require temperature cycling in order to dissociate the target from the synthesized strand. In this method, a single temperature may be employed after denaturation has occurred. The temperature of the reaction should be high enough to set a level of stringency that minimizes non-specific binding but low enough to allow specific hybridization to the target strand. In addition proper temperature should support efficient enzyme activity. From about 37° C. to about 42° C. has been found to be a preferred temperature range. Denaturation of the enzymes and nucleic acid is to be avoided. The mixture comprising the reaction components for target generation and SDA can optionally include NMP (1-methyl 2 pyrrolidinone), glycerol, poly (ethylene glycol), dimethyl sulfoxide and/or formamide. The inclusion of such organic solvents is believed to help alleviate background hybridization reactions.

Referring to FIG. 1, one example of this invention is set forth. In this example, the strand labelled P represents the primer and contains at the 5' end the sequence CCGGG which is recognized by the endonuclease NciI. The strand labelled T is the target sequence which has already been fragmented and rendered single stranded. In the method, the primer binds to the target and in the presence of polymerase, deoxynucleoside triphosphates and α-thio substituted deoxycytosine triphosphate, the primer is extended the length of the target while the target is extended through the recognition sequence. In the presence of the endonuclease NciI, the primer strand is nicked between the C-G residues. In the presence of the polymerase lacking 5' to 3' exonuclease activity, the 3' end at the nick is extended, the downstream the primer strand is displaced from the target strand beginning at the nick, and a new strand is synthesized. The displaced downstream primer strand is the amplification reaction product. In summary fashion (not shown), the newly synthesized strand will also be nicked by the endonuclease and the polymerase will then displace this strand, generating another amplification reaction product. This process continues until the reaction is stopped or one of the reagents becomes limiting.

Figure 2:
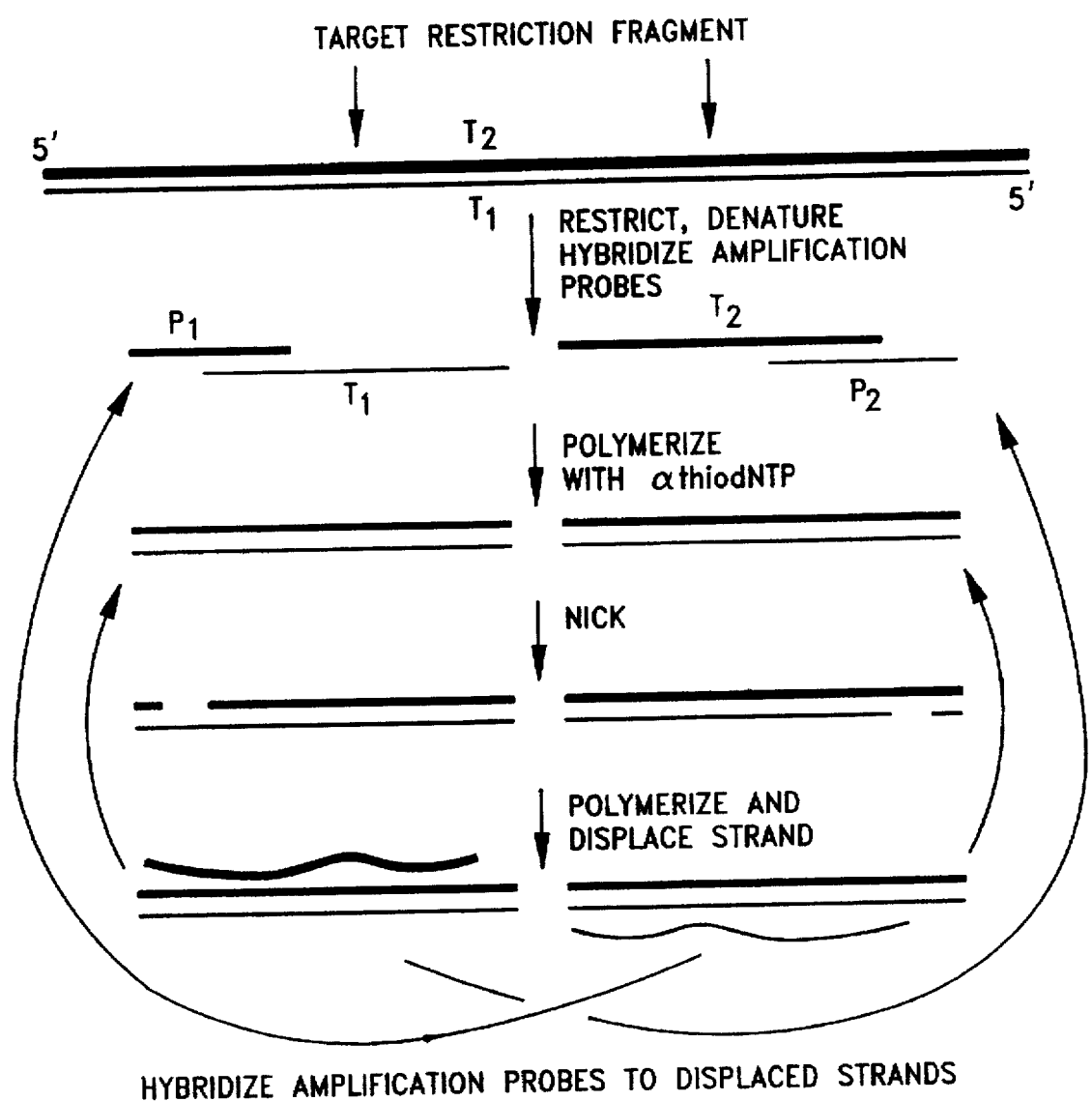
FIG. 2 comprises a flow chart of the steps in an example of the method claimed in this invention for double stranded genomic DNA and two amplification primers.

FIG. 2 depicts Strand Displacement Amplification (SDA) using two primers. The first step is to generate a target DNA fragment with defined 5'- and 3'-ends (e.g., by restriction enzyme cleavage). Following heat denaturation, the two single-stranded target fragments ($T_1$ and $T_2$) bind respectively to the two SDA primers ($P_1$ and $P_2$) which are present in excess. The 5'-overhangs of $P_1$ and $P_2$ contain a recognition sequence for the nicking enzyme. DNA polymerase extends the 3'-ends of the duplexes using four deoxynucleosidetriphosphates, including at least one modified deoxynucleotide triphosphate, producing hemimodified recognition sites on $P_1T_1$ and $P_2T_2$. The nicking enzyme nicks the unprotected primer strands of the hemimodified recognition sites, leaving intact the modified complementary strands. DNA polymerase extends the 3'-end at the nick on $P_1T_1$ and displaces the downstream strand, which is functionally equivalent to $T_2$. Likewise, extension at the nick on $P_2T_2$ results in displacement of a downstream strand which is functionally equivalent to $T_1$. Nicking, polymerization and displacement steps cycle continuously on $P_1T_1$ and $P_2T_2$ because extension at a nick regenerates a nickable recognition site. Target amplification is exponential because strands displaced from $P_1T_1$ serve as target for $P_2$ while strands displaced from $P_2T_2$ serve as target for $P_1$. These steps continuously repeat over the course of amplification. For example, $10^6$-fold amplification theoretically derives from about 20 repetitions or cycles of the steps in FIG. 2 ($2^{20}=10^6$). Sense and antisense DNA strands are differentiated by thin and thick lines.

SDA can be used to generate single-stranded DNA probes or single-stranded templates for sequencing. Toward this goal, SDA operates either with a single primer (FIG. 1) or using two primers (FIG. 2) wherein one primer is in excess over the other. The result is excess production of one displaced single strand over the other.

The presence of the amplified target can then be detected by any number of methods. One method is to detect reaction products of a specific size by means of gel electrophoresis. This method is particularly useful when the nucleotides used are labelled with a radio-label, such as $^{32}P$. Other methods include labelling the nucleotides with a physical label, such as biotin. Biotin-containing reaction products can then be identified by means of avidin bound to a signal generating enzyme, such as peroxidase. Detection systems useful in the practice of this invention comprise homogeneous systems, which do not require separation, and heterogeneous systems. In each system, one or more detectable markers are used and the reaction or emission from the detection system is monitored, preferably by automated means. Examples of homogeneous systems include fluorescence polarization, enzyme mediated immunoassays, fluorescence energy transfer, hybridization protection (e.g., acridinium luminescence) and cloned enzyme donor immunoassays. Examples of heterogeneous systems include enzyme labels (such as peroxidase, alkaline phosphatase and beta-galactosidase), fluorescent labels (such as enzymatic labels and direct fluorescence labels (e.g., fluorescein and rhodamine), chemiluminescence and bioluminescence. Liposomes or other sac like particles also can be filled with dyes and other detectable markers and used in such detection systems. In these systems, the detectable markers can be conjugated directly or indirectly to a capture moiety or the amplified products can be generated in the presence of a receptor which can be recognized by a ligand for the receptor.

The following examples illustrate the specific embodiments of the invention described herein. As would be apparent to skilled artisans, various changes and modifications are possible and are contemplated within the scope of the invention described.

EXAMPLE 1

This example illustrates SDA using a FokI restriction step to generate target fragments prior to amplification. Two primers were synthesized on an Applied BioSystems 380B instrument using phosphoramidite chemistry and 3'-amine-ON CPG columns (Clontech Laboratories, Palo Alto, Calif.) which incorporate a primary amine at the 3' terminus. Nucleotides were ammonium deprotected and purified by denaturing gel electrophoresis. The primer sequences were SEQ ID NO: 1 and SEQ ID NO: 2.

Plasmid pBR322 (Boerhinger Mannheim, Indianapolis, Ind.) was serially diluted with 0.05 mg/ml *E. coli* DNA, 50 mM K acetate, 10 mM Mg acetate, 1 mM DTT, 12.5 mM TRIS (pH 7.9) at 25° C. Twenty µl samples containing 1 µg *E. coli* DNA and various amounts of pBR322 were digested 3 hours at 37° C. with 10 Units of FokI (New England Biolabs, Beverly, Mass.). The FokI digests of pBR322/*E. coli* DNA were diluted to 100 µl in the presence of 12.5 mM K acetate, 10 mM Mg acetate, 1 mM DTT, 12.5 mM TRIS (pH 7.9) at 25° C., 100 µg/ml BSA, 0.3 mM each of dATP, dGTP, TTP, dCTP($\alpha$S) (Pharmacia, Piscataway, N.J.) and 0.1 µM of each primer. One set of samples underwent Strand Displacement Amplification for 4 hours at 45° C. upon addition of 4 Units 5'→3' exonuclease deficient Klenow fragment of DNA polymerase I (US Biochemical, Cleveland, Ohio) and 48 Units NciI (New England Biolabs). A second set of samples were run without the polymerase and without NciI as unamplified standards.

To detect the reaction products, a pBR322 specific detection probe, SEQ ID NO: 3, was prepared and was labelled with $^{32}P$ using polynucleotide kinase. Ten µl aliquots of the amplified and unamplified Fok I/pBR322/*E. coli* DNA samples were mixed with 2 µl of 1.8 µM $^{32}P$ labelled detection probe, 0.5 Units/µl Taq DNA polymerase (United States Biochemical). Samples were heated for 2 minutes at 95° C., 5 minutes at 50° C., quenched with 50% urea, and a portion was loaded onto a 10% denaturing polyacrylamide gel. The presence of amplified reaction products was detected through extension of the $^{32}P$ labelled detection probe to a length of 43 or 60 nucleotides. Unamplified FokI/pBR322 was indicated by extension to 40 nucleotides. Electrophoresis $^{32}P$ labelled bands were quantified by liquid scintillation counting subtracting appropriate background bands. The results are shown in TABLE I.

TABLE I

| # pBR32 Molecules | Amplified (±50 cpm) | Unamplified (±50 cpm) |
|---|---|---|
| $3 \times 10^8$ | 52900 | 215 |
| $3 \times 10^7$ | 18200 | 24 |
| $3 \times 10^6$ | 5690 | 21 |
| $3 \times 10^5$ | 298 | 0 |
| 0 | 37 | ND |

ND = not determined

As can be seen from TABLE I, as the amount of pBR322 DNA in the aliquot decreases, the number of counts per minute (CPM) also decreases.

EXAMPLE 2

This example illustrates SDA using a synthetic single stranded target DNA sequence. A synthetic nucleic acid target was constructed having the sequence of SEQ ID NO: 4. Primers for strand displacement amplification reaction using the restriction enzyme HincII (New England BioLabs) were synthesized to provide a 3'-NH$_2$ cap using 3'-amine-ON CPG columns. The primer sequences used were SEQ ID NO: 5 and SEQ ID NO: 6. A probe for the detection of the reaction products was of the sequence: SEQ ID NO: 7. All synthetic sequences were synthesized on an Applied Biosystems 380B instrument as above, and were gel purified on 10% or 15% polyacrylamide gels containing 50% urea. Excised bands were electroeluted in 1/2X TBE buffer.

SEQ ID NO: 4 was diluted into 0.3 μM of the primers (i.e., SEQ ID NO: 5 and SEQ ID NO: 6) to provide a final stock concentration of 600,000 molecules of target/μl. This mixture was boiled for 3 minutes and placed at 37° C. Serial 4 fold dilutions of this stock solution were then prepared in the presence of the primers. (In the control, only amplification primers were present.) Twenty μl of the diluted stock target solutions were added to a mixture to provide a final volume of 60 ml and a final concentration of the following components: 20 mM TRIS (pH 7.2) at 25° C., 0.1 μM of the primer sequences, 20 mM ammonium sulfate, 50 mM KCl, 50 Units HincII, 5 Units exo⁻Klenow polymerase (US Biochemical), 1 mM DTT, 5 mM $MgCl_2$, and 300 μM each of 5'dCTP, 5'dGTP, 5'dTTP and 5'dATP(αS). The amplification reaction was allowed to proceed at 37° C. for 1 or 2 hours. In one reaction set, an additional 50 Units of HincII was added after 1 hour and the reaction was allowed to proceed for an additional hour.

At the end of the reaction times, a 10 μl aliquot of each mixture was placed on ice. To this 10 μl was added 1 μl of a 1 μM stock solution of capture probe freshly labelled with $^{32}$P. This mixture was boiled for 3 minutes and cooled to 37° C., whereupon 1 μl of 1 Unit/μl of Sequenase 2.0 (U.S. Biochemical) was added. (This enzyme will polymerize the capture probe along the full length of any reaction product when the capture probe is bound to a reaction product.) This extension reaction was allowed to proceed for 15 minutes at 37° C. To this mixture was added an equal volume of loading dyes in 50% urea. Samples were boiled again for 3 minutes before loading onto a 10% polyacrylamide gel containing 50% urea. Samples loaded on the gel represented 2.5 μl of the original 60 μl reaction mixture. Electrophoresis was allowed to proceed for 1 to 1.5 hours at 59 W after which the gel was removed and placed on film overnight at −70° C. Bands were rendered visible after exposure, were excised and quantified by liquid scintillation.

TABLE II

| # Target | 1 Hour (cpm) | 2 Hour (cpm) | 2 Hour with Additional HincII (cpm) |
|---|---|---|---|
| 0 | 0 | 0 | 0 |
| 2000 | ND | 2 | 8 |
| 8000 | 4 | 12 | 36 |
| 30,000 | 37 | 78 | 129 |
| 125,000 | 175 | 196 | 746 |
| 500,000 | 824 | 1858 | 2665 |

Referring to TABLE II, it can be seen that SDA clearly distinguishes between 0 and 30000 initial targets.

EXAMPLE 3

This is an example using a FokI restriction digest prior to SDA. The following primer sequences were used: SEQ ID NO: 8 and SEQ ID NO: 9. These sequences were generated as in the other examples and were used to detect a target sequence in the plasmid pBR322.

One μg of pBR322 was digested for 2 hours at 37° C. with 8 Units of Fok I, and then was serially diluted with 0.05 mg/ml human placental DNA digested with HphI, 50 mM KCl, 5 mM $MgCl_2$, 20 mM $(NH_4)_2SO_4$, 1 mM DTT and 20 mM TRIS (pH 7.2 at 25° C.). Ten μl samples containing 0.5 μg human placental DNA and various amounts of pBR322 were diluted to 100 μl in the presence of 50 mM KCl, 5 mM $MgCl_2$, 20 mM $(NH_4)_2SO_4$, 1 mM DTT and 20 mM TRIS (pH7.2 at 25° C.) 100 μg/ml BSA, 0.1 mM each of dGTP, TTP, dCTP (Pharmacia), 0.5 mM dATP(αS) (Pharmacia) and 0.1 μM of each probe. One set of samples underwent Strand Displacement Amplification for 3.5 hours at 39° C. upon addition of 5 Units of 5'→3' exonuclease deficient Klenow fragment of DNA polymerase I and 50 Units of HincII. A second set of samples were run without polymerase and without HincII as unamplified standards.

To detect the reaction products, the pBR322 detection primer having SEQ ID NO: 7 was used having been labelled with $^{32}$P. Ten ml aliquots of the amplified and unamplified Fok I/pBR322/human placental DNA samples were mixed with 2 μl of 1 μM $^{32}$P labelled detection primer, and were heated 2 minutes at 95° C. Two Units of Sequenase 2.0 were then added, and samples were incubated for 5 minutes at 37° C. Samples were quenched with 50% urea and loaded onto a 10% denaturing polyacrylamide gel. The presence of amplified reaction products was detected through extension of the $^{32}$P labelled detection primer to lengths of 54 and 75 nucleotides. Unamplified samples were indicated by extension to 50 nucleotides. Electrophoresis of the labelled bands was quantified by liquid scintillation counting subtracting appropriated background bands. The results are shown in TABLE III.

TABLE III

| # pBR32 Molecules | Amplified (±10 cpm) | Unamplified (±10 cpm) |
|---|---|---|
| $10^9$ | ND | 1963 |
| $10^8$ | ND | 257 |
| $10^7$ | ND | ND |
| $10^6$ | 135408 | ND |
| $10^5$ | 13841 | ND |
| $10^4$ | 2324 | ND |
| $10^3$ | 380 | ND |
| 0 | 139* | ND |

ND = not determined
*The amplified sample with zero added pBR322 molecules exhibited faint amplified target specific bands (54- and 75-mer) due to inadvertent contamination with pBR322.

Comparing the unamplified samples with $10^9$ and $10^8$ pBR322 molecules with respective samples containing $10^4$ and $10^3$ pBR322 molecules indicates an amplification factor of over $10^5$ fold. Further, it has been found that by adjusting the buffer composition and deoxynucleoside triphosphate concentrations one can improve amplification performance. Inclusion of $(NH_4)_2SO_4$, a relatively low pH and a dATP (αS):dGTP ratio of 5:1 have been found to enhance amplification efficiency.

EXAMPLE 4

Strand Displacement Amplification was performed essentially as in Example 2, substituting 5'Me(dCTP) as the modified deoxynucleoside triphosphate and ScrfI or Fnu4HI as the restriction endonuclease. SEQ ID NO: 4 was used as the target sequence. As ScrfI is an isoschizomer of NciI, SEQ ID NO: 1 and SEQ ID NO: 2 were used as amplification primers in the ScrfI amplification reactions. SEQ ID NO: 10 and SEQ ID NO: 11 were the amplification primers used in the Fnu4HI amplification reactions with SEQ ID NO: 4 as the target. Bst polymerase was substituted for exo⁻Klenow polymerase. Amplification in the presence of dCTP(αS) was analyzed for comparison. After gel electrophoresis, the extent of amplification was determined visually by autoradiography.

Fnu4HI supported levels of amplification which were slightly less than in the HincII/dATP(αS) system using either 5'Me(dCTP) or dCTP(αS). ScrfI supported low levels of amplification when dCTP(αS) was the modified deoxynucleoside triphosphate, but amplification was increased in the presence of 5'Me(dCTP).

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference. It will be apparent to one of ordinary skill in the art that many changes and modifications can be made in the invention without departing from the spirit or scope of the appended claims.

What is claimed is:

1. A method for amplifying a target nucleic acid sequence comprising:
   a) providing a single stranded nucleic acid fragment containing the target nucleic acid sequence, the fragment having a 5' end and a 3' end;
   b) binding an oligonucleotide primer to the 3' end of the fragment such that the primer forms a 5' single stranded overhang, the primer comprising a 3' end complementary to the 3' end of the fragment and a 5' end comprising a recognition sequence for a restriction endonuclease which does not cut the target nucleic acid sequence;
   c) extending the primer on the fragment in the presence of
      i) a DNA polymerase lacking 5'-3' exonuclease activity,
      ii) deoxynucleoside triphosphates,
      iii) at least one substituted deoxynucleoside triphosphate, and
      iv) a restriction endonuclease which nicks the recognition sequence when the recognition sequence is double stranded and hemimodified by incorporation of the substituted deoxynucleoside triphosphate,
   thereby producing a double stranded first reaction product comprising the primer, a first newly synthesized strand and a hemimodified restriction endonuclease recognition sequence;
   d) nicking the double stranded hemimodified restriction endonuclease recognition sequence with the restriction endonuclease;
   e) extending from the nick using the polymerase, thereby displacing the first newly synthesized strand from the first reaction product and generating a second newly synthesized strand, and;
   f) repeating the nicking, extending and displacing steps such that the target sequence is amplified.

2. The method of claim 1 further comprising detecting the presence of the amplified target sequence.

3. The method of claim 1 wherein the nucleic acid fragment containing the target sequence is double-stranded and is rendered single stranded before step b).

4. A method for amplifying a target nucleic acid sequence comprising:
   a) providing a double stranded nucleic acid fragment containing the target nucleic acid sequence;
   b) denaturing the double stranded fragment to produce a first single stranded fragment having a 5' end and a 3' end and a second single stranded fragment having a 5' end and a 3' end;
   c) binding a first oligonucleotide primer to the 3' end of the first single stranded fragment and a second oligonucleotide primer to the 3' end of the second single stranded fragment such that the first and second primers form 5' single stranded overhangs on the first and second single stranded fragments, respectively, the first and second primers each comprising a 3' end complementary to the 3' end of the first or second single stranded fragment and a 5' end comprising a recognition sequence for a restriction endonuclease which does not cut the target nucleic acid sequence;
   d) extending the first and second primers on the first and second single stranded fragments, respectively, in the presence of
      i) a DNA polymerase lacking 5'-3' exonuclease activity,
      ii) deoxynucleoside triphosphates,
      iii) at least one substituted deoxynucleoside triphosphate, and
      iv) a restriction endonuclease which nicks the recognition sequence when the recognition sequence is double stranded and hemimodified by incorporation of the substituted deoxynucleoside triphosphate,
   thereby producing a double stranded first reaction product comprising the first primer, a first newly synthesized strand and a first hemimodified restriction endonuclease recognition sequence and a double stranded second reaction product comprising the second primer, a second newly synthesized strand and a second hemimodified restriction endonuclease recognition sequence;
   e) nicking the first and second hemimodified restriction endonuclease recognition sites with the restriction endonuclease;
   f) extending from the nicks using the polymerase, thereby displacing the first newly synthesized strand from the first reaction product and displacing the second newly synthesized strand from the second reaction product and generating a third and a fourth newly synthesized strand, respectively;
   g) repeating the nicking, extending and displacing steps such that the target sequence is amplified.

5. The method of claim 4 wherein the first and second single stranded fragments are produced by heating the double stranded fragment.

6. The method of claim 4 further comprising detecting the amplified target sequence.

7. The method of claim 6 wherein the amplified target sequence is detected by means of a label selected from the group consisting of a radiolabel, an enzyme and a fluorescent dye.

8. The method of claim 4 wherein the polymerase is selected from the group consisting of the Klenow fragment of DNA polymerase I, the exonuclease deficient Klenow fragment of DNA polymerase I, T5 DNA polymerase, Phi29 DNA polymerase and the Klenow fragment of Bst polymerase.

9. The method of claim 8 wherein the polymerase is the exonuclease deficient Klenow fragment of DNA polymerase I.

10. The method of claim 8 wherein the double stranded fragments are prepared by use of a restriction enzyme.

11. A method for amplifying a target nucleic acid sequence comprising:
    a) providing a single stranded nucleic acid fragment containing the target nucleic acid sequence, the fragment having a 5' end and a 3' end;
    b) binding an oligonucleotide primer to the 3' end of the fragment such that the primer forms a 5' single stranded overhang, the primer comprising a 3' end complementary to the 3' end of the fragment and a 5' end comprising a recognition sequence for a restriction endonuclease which does not cut the target nucleic acid sequence;

c) extending the primer on the fragment in the presence of
i) a DNA polymerase lacking 5'-3' exonuclease activity,
ii) deoxynucleoside triphosphates,
iii) at least one methyl-substituted deoxynucleoside triphosphate, and
iv) a restriction endonuclease which nicks the recognition sequence when the recognition sequence is double-stranded and hemimodified by incorporation of the methyl-substituted deoxynucleoside triphosphate, thereby producing a double stranded first reaction product comprising the primer, a first newly synthesized strand and a hemimodified restriction endonuclease recognition sequence;

d) nicking the double stranded hemimodified restriction endonuclease recognition sequence with the restriction endonuclease;

e) extending from the nick using the polymerase, thereby displacing the first newly synthesized strand from the first reaction product and generating a second newly synthesized strand, and;

f) repeating the nicking, extending and displacing steps such that the target sequence is amplified.

12. The method of claim 11 further comprising detecting the amplified target sequence.

13. The method of claim 12 wherein the amplified target sequence is detected by means of a detectable label.

14. The method of claim 13 wherein the label is selected from the group consisting of a radiolabel, an enzyme and a fluorescent dye.

15. The method of claim 14 wherein detection is carried out in a solid phase system.

16. The method of claim 11 wherein the target sequence is contained in a double stranded nucleic acid fragment which is rendered single stranded before step b).

17. The method of claim 16 wherein the double stranded fragment is prepared by use of a restriction enzyme.

18. The method of claim 17 wherein the restriction enzyme is the same as the restriction endonuclease.

19. The method of claim 17 wherein the single stranded fragment is produced by heating the double stranded fragment.

20. The method of claim 11 wherein the restriction endonuclease is selected from the group consisting of Fnu4HI and ScrfI.

21. A method for amplifying a target nucleic acid sequence comprising:
a) providing a single stranded nucleic acid fragment containing the target nucleic acid sequence, the fragment having a 5' end and a 3' end;
b) binding an oligonucleotide primer to the 3' end of the fragment such that the primer forms a 5' single stranded overhang, the primer comprising a 3' end complementary to the 3' end of the fragment and a 5' end comprising a recognition sequence for a restriction endonuclease which does not cut the target nucleic acid sequence;
c) extending the primer on the fragment in the presence of
i) a DNA polymerase lacking 5'-3' exonuclease activity,
ii) deoxynucleoside triphosphates,
iii) at least one substituted deoxynucleoside triphosphate, and
iv) a restriction endonuclease which nicks the recognition sequence when the recognition sequence is double stranded and hemimodified by incorporation of the substituted deoxynucleoside triphosphate, thereby producing a double stranded first reaction product comprising a hemimodified restriction endonuclease recognition sequence;

d) nicking the double stranded hemimodified restriction endonuclease recognition sequence with the restriction endonuclease;

e) extending from the nick using the polymerase, thereby displacing a copy of the target sequence, and;

f) repeating the nicking, extending and displacing steps such that the target sequence is amplified.

22. The method of claim 21 further comprising detecting the amplified target sequence.

23. The method of claim 21 wherein the polymerase is selected from the group consisting of the Klenow fragment of DNA polymerase I, the exonuclease deficient Klenow fragment of DNA polymerase I, T5 DNA polymerase, Phi29 DNA polymerase and the Klenow fragment of Bst polymerase.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
TCATTTCTTA CTTTACCGGG AAAAATCACT CAGGGTCAA                    39
```

( 2 ) INFORMATION FOR SEQ ID NO:2:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
TCATTTCTTA CTTTACCGGG ACCCTGTGGA ACACCTACAT                   40
```

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CCAGCGCTTC GTTAATACA                                          19
```

( 2 ) INFORMATION FOR SEQ ID NO:4:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
ACCCTGTGGA ACACCTACAT CTGTATTAAC GAAGCGCTGG CATTGACCCT        50

GAGTGATTTT TC                                                 62
```

( 2 ) INFORMATION FOR SEQ ID NO:5:

( i ) SEQUENCE CHARACTERISTICS:
        ( A ) LENGTH: 33 base pairs (B) TYPE: nucleic acid
        (C) STRANDEDNESS: single
        (D) TOPOLOGY: linear (x i) SEQUENCE DESCRIPTION: SEQ ID NO:5:

GGATATTTAT TGTTGACTTA CCCTGTGGAA CAC                33

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (x i) SEQUENCE DESCRIPTION: SEQ ID NO:6:

GGAATAATAA TATGTTGACT TGAAAAATCA CTCAG              35

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO:7:

ACATCTGTAT TAACGAAGCG                               20

(2) INFORMATION FOR SEQ ID NO:8:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (x i) SEQUENCE DESCRIPTION: SEQ ID NO:8:

TTGAAGTAAC CGACTATTGT TGACTACCCT GTGGAACACC T       41

(2) INFORMATION FOR SEQ ID NO:9:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (x i) SEQUENCE DESCRIPTION: SEQ ID NO:9:

TTGAATAGTC GGTTACTTGT TGACTCAGAG AAAAATCACT CAG     43

(2) INFORMATION FOR SEQ ID NO:10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (x i) SEQUENCE DESCRIPTION: SEQ ID NO:10:

GGATATTTAT TTATTGCGG CTTACCCTGT GGAACAC             37

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single (D) TOPOLOGY: linear (xi) SEQUENCE DESCRIPTION: SEQ ID NO:11:

GGAATAAATA AATATGCGGC TTGAAAAATC ACTCAG    36